United States Patent [19]
Maarschalkerweerd

[11] Patent Number: 5,504,335
[45] Date of Patent: Apr. 2, 1996

[54] FLUID TREATMENT DEVICE AND METHOD

[75] Inventor: Jan M. Maarschalkerweerd, Ontario, Canada

[73] Assignee: Trojan Technologies, Inc., London, Canada

[21] Appl. No.: 323,808

[22] Filed: Oct. 17, 1994

[51] Int. Cl.$^6$ .................................................. G01N 21/05
[52] U.S. Cl. ........................... 250/435; 250/436; 422/24; 210/748
[58] Field of Search ..................... 250/428, 432 R, 250/435, 436; 422/22, 24; 210/748

[56] References Cited

U.S. PATENT DOCUMENTS

| | | |
|---|---|---|
| 2,413,704 | 1/1947 | Glatthar et al. . |
| 2,670,439 | 2/1954 | Darney . |
| 3,061,721 | 10/1962 | Brenner . |
| 3,182,191 | 5/1965 | Ellner et al. . |
| 3,456,107 | 7/1969 | Robertson . |
| 4,017,734 | 4/1977 | Ross ........................................ 250/435 |
| 4,467,206 | 8/1984 | Taylor et al. ............................ 250/435 |
| 4,482,809 | 11/1984 | Maarschalkerweerd ................ 250/436 |
| 4,602,162 | 7/1986 | Sperry ..................................... 250/436 |
| 4,694,179 | 9/1987 | Lew et al. ................................ 422/24 |
| 4,757,205 | 7/1988 | Latel et al. .............................. 250/435 |
| 4,767,932 | 8/1988 | Ellner ....................................... 250/435 |
| 4,872,980 | 10/1989 | Maarschalkerweerd ................ 210/243 |
| 4,922,114 | 5/1990 | Boehme ................................... 250/435 |
| 4,963,750 | 10/1990 | Wilson ..................................... 250/436 |
| 5,006,244 | 4/1991 | Maarschalkerweerd ................ 210/243 |
| 5,019,256 | 5/1991 | Ifill et al. ................................. 210/232 |
| 5,091,152 | 2/1992 | Thomas, Sr. ............................. 422/22 |
| 5,124,131 | 6/1992 | Wekhof ................................. 422/186.3 |
| 5,200,156 | 4/1993 | Wedekamp ............................... 422/24 |
| 5,227,140 | 7/1993 | Hager et al. .......................... 422/186.3 |
| 5,266,215 | 11/1993 | Engelhard ............................... 210/748 |
| 5,368,748 | 11/1994 | Sanderson ................................ 422/22 |

FOREIGN PATENT DOCUMENTS

| | | |
|---|---|---|
| 421296 | 1/1912 | France . |
| 434069 | 1/1921 | France . |
| 855521 | 7/1949 | Germany . |
| 2213658 | 3/1972 | Germany . |
| 2732859 | 2/1979 | Germany ............................... 250/435 |
| 3441535 | 11/1984 | Germany . |
| 0266965 | 4/1989 | Germany ............................... 422/24 |

OTHER PUBLICATIONS

"Die Katadyn UV-Verfahren zur Keimreduktior im Abwasser" Article, Oct. 1990, Katadyn Co., Germany, 10 pages.
UVPS UV Module Schematic, Lebanon, MO, Believed to be Installed Jul. 1988, one page.

Primary Examiner—Jim Beyer
Assistant Examiner—James Beyer
Attorney, Agent, or Firm—Fitzpatrick, Cella, Harper & Scinto

[57] ABSTRACT

A fluid treatment device comprising a housing for receiving a flow of fluid, the housing comprising a fluid inlet, a fluid outlet, a fluid treatment zone disposed between the fluid inlet and the fluid outlet, and at least one radiation source module disposed in the fluid treatment zone, the at least one radiation source module comprising a radiation source sealably connected to a leg, the leg sealably mounted to the housing, the radiation source being disposed substantially parallel to the flow of fluid. A method of treating a fluid in a housing comprising a fluid inlet, a fluid outlet, a fluid treatment zone disposed between the fluid inlet and the fluid outlet, the fluid treatment zone having at least one radiation source disposed therein is also described. The method comprises the steps of: (i) providing a flow of the fluid to the fluid inlet; (ii) feeding the flow of fluid from the fluid inlet to the fluid treatment zone in a manner substantially parallel to the at least one radiation source; (iii) irradiating the flow of fluid in the fluid treatment zone; and (iv) feeding the flow of fluid to the fluid outlet. During the method, the flow of fluid through the fluid inlet, the fluid outlet and the fluid treatment zone is substantially collinear. The fluid treatment device and method are ideally suited (but not limited) to inactivate microorganisms present in water.

28 Claims, 6 Drawing Sheets

FLUID TREATMENT DEVICE AND METHOD

FIELD OF THE INVENTION

In one of its aspects, present invention relates to a fluid treatment device. In another of its aspects, the present invention relates to method for treating a fluid.

BACKGROUND OF THE INVENTION

Fluid treatment devices and systems are known. For example, U.S. Pat. Nos. 4,482,809, 4,872,980 and 5,006,244, and U.S. patent application Ser. No. 08/026,572, now U.S. Pat. No. 5,418,370 (all assigned to the assignee of the present invention), the contents of each of which are hereby incorporated by reference, all describe gravity fed fluid treatment systems which employ ultraviolet (UV) radiation to inactivate microorganisms present in the fluid.

The devices and systems described in the '809, '980 and '244 patents generally include several UV lamps each of which are mounted within sleeves extending between two support arms of the frames. The frames are immersed into the fluid to be treated which is then irradiated as required. The amount of radiation to which the fluid is exposed is determined by the proximity of the fluid to the lamps. One or more UV sensors may be employed to monitor the UV output of the lamps and the fluid level is typically controlled, to some extent, downstream of the treatment device by means of level gates or the like. Since, at higher flow rates, accurate fluid level control is difficult to achieve in gravity fed systems, fluctuations in fluid level are inevitable. Such fluctuations can lead to non-uniform irradiation in the treated fluid.

However, disadvantages exist with the above-described systems. Depending on the quality of the fluid which is being treated, the sleeves surrounding the UV lamps periodically become fouled with foreign materials, inhibiting their ability to transmit UV radiation to the fluid. When fouled, at intervals which may be determined from historical operating data or by the measurements from the UV sensors, the sleeves must be manually cleaned to remove the fouling materials. Regardless of whether the UV lamp frames are employed in an open, channel-like system or a closed system, cleaning of the sleeves is impractical.

In open, channel-like systems, the modules comprising the sleeves are usually removed from the channel and immersed in a separate tank containing a suitable cleaning fluid. In closed systems, the device must be shut down and the sleeves are thereafter cleaned by charging with a suitable cleaning fluid or by removal of the lamps in the manner described for the open, channel-like system. In either type of systems the operator must accept significant downtime of the system and/or invest significant additional capital to have in place sufficient redundant systems with appropriate control systems to divert the flow of fluid from the systems being cleaned.

The system described in the '572 application is a significant advance in the art in that it obviates a number of disadvantages deriving from the devices and systems disclosed in the '809, '980 and '244 patents. Unfortunately, the system described in the '572 application is ideally suited for use in an open, channel-like system and is not readily adaptable to be used in a completely closed system where the flow of fluid is fed under pressure in a pipe.

It would be desirable to have a fluid treatment device which could be readily adapted to be treat a flow of fluid fed under pressure in a pipe or like enclosure. It would be further desirable if such a device was relatively easy to clean or keep clean during use.

SUMMARY OF THE INVENTION

It is an object of the present invention to provide a novel fluid treatment device which obviates or mitigates at least one of the disadvantages of the prior art.

It is another object of the present invention to provide a novel method for treating a fluid which obviates or mitigates at least one of the disadvantages of the prior art.

Accordingly, in one of its aspects, the present invention provides a fluid treatment device comprising a housing for receiving a flow of fluid, the housing comprising a fluid inlet, a fluid outlet, a fluid treatment zone disposed between the fluid inlet and the fluid outlet, and at least one radiation source module disposed in the fluid treatment zone, the at least one radiation source module comprising a radiation source sealably connected to a leg, the leg sealably mounted to the housing, the radiation source being disposed substantially parallel to the flow of fluid.

In another of its aspects, the present invention provides a method of treating a fluid in a housing comprising a fluid inlet, a fluid outlet, a fluid treatment zone disposed between the fluid inlet and the fluid outlet, the fluid treatment zone having at least one radiation source disposed therein, the method comprising the steps of:

(i) providing a flow of the fluid to the fluid inlet;

(ii) feeding the flow of fluid from the fluid inlet to the fluid treatment zone in a manner substantially parallel to the at least one radiation source;

(iii) irradiating the flow of fluid in the fluid treatment zone; and (iv) feeding the flow of fluid to the fluid outlet;

wherein the flow of fluid through the fluid inlet, the fluid outlet and the fluid treatment zone is substantially colinear.

Thus, the present fluid treatment device and method relate to a closed system for treatment of a fluid. As used throughout this specification, the term "closed system", in relation to treatment of a fluid, is intended to encompass a system in which the flow of fluid is pressurized and substantially completely contained in an enclosure throughout treatment. Thus, open, channel-like systems are outside the scope of the present invention since, in the operation of such systems the level of water in the channel and/or treatment zone can vary. The source of pressurization of the flow of fluid is not particularly restricted. For example, the pressure can be generated by a pump or by the action of gravity.

Ideally, the present fluid treatment device and method may be used "in-line" in conventional water piping. Depending on the particular application, the piping can be up to 4 in. diameter for domestic applications, or 1 ft. to 3 ft. diameter or more for municipal applications.

BRIEF DESCRIPTION OF THE DRAWINGS

Embodiments of the present invention will be described with reference to the accompanying drawings, in which.

In the Figures, like reference numerals from one Figure to another are intended to designated like parts.

DETAILED DESCRIPTION OF THE PREFERRED EMBODIMENTS

For clarity, a brief description of a prior art, closed system, fluid treatment device will be presented before discussing the present invention.

Figure 1:
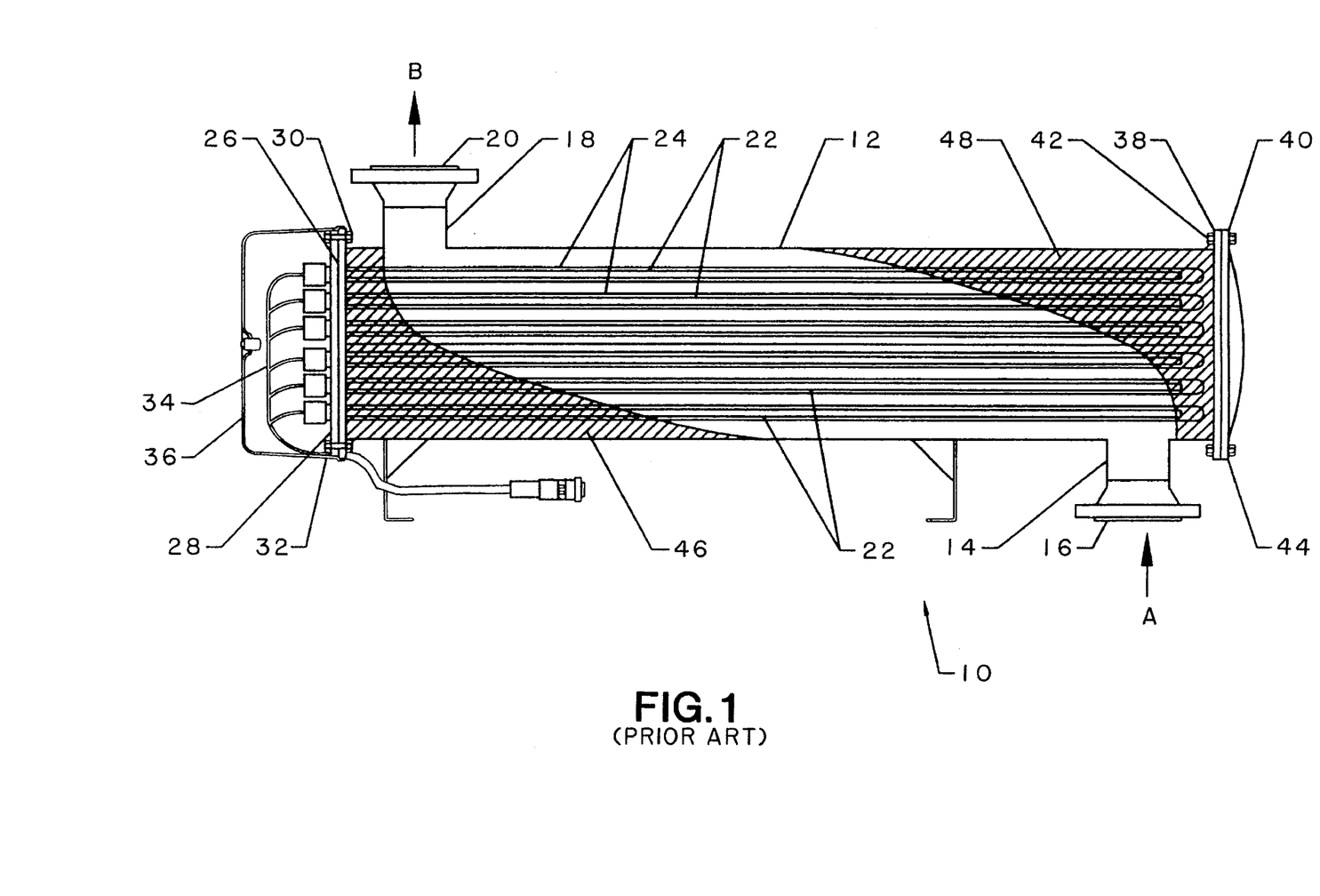
FIG. 1 illustrates a side elevation, partially cut away, of a conventional closed system for treatment of a fluid.

FIG. 1 illustrates such a device which is conventionally available. Thus, with reference to FIG. 1, there is illustrated a fluid treatment device 10 having a housing 12. Housing 12 comprises a fluid inlet 14 having an inlet flange 16 and a fluid outlet 18 having an outlet flange 20. Contained within housing 12 is a plurality of ultraviolet (UV) lamps 22, with each lamp surrounded by a quartz sleeve 24. Housing 12 comprises a first flange 26 to which is connected a first plate 28. The connection between first flange 26 and first plate 28 is made by a number of bolt/nut combinations 30, 32 and a seal (not shown) to achieve a hermetic seal. First plate 28 is adapted to permit the emergence of a wire 34 from each UV lamp 22. A boot 36 is connected to first plate 28 allows emergence of each wire 34. Each wire 34 is connected to a power supply (not shown) and control system (not shown) in a conventional manner. Housing 12 further comprises a second flange 38 to which is connected a second plate 40. The connection between second flange 38 and second plate 40 is made by a number of bolt/nut combinations 42, 44 and a seal (not shown) to achieve a hermetic seal. The exact manner (not shown) by which the seals between first flange 26 and first plate 28, and second flange 38 and second plate 40, respectively, are achieved is within the purview of a person skilled in the art.

In use, inlet flange 16 is connected to a suitable supply pipe (not shown) and outlet flange 20 is connected to a suitable return pipe (not shown). As depicted by arrow A, fluid to be treated enters housing 12 via fluid inlet 14. The fluid is exposed to radiation from UV lamps 22 and exits housing 12 via fluid outlet 18 as depicted by arrow B.

The design of fluid treatment device 10 is such that it suffers from significant hydraulic head loss due to the fact that (i) the cross-sectional area of fluid inlet 14 and the fluid outlet 20 of housing 12 is significantly less than that of housing 12, and (ii) the flow of fluid flows a relatively tortuous path. This leads to the creation of dead zones 46, 48 within housing 12 wherein the flow of fluid is negligible resulting in inefficient and, in some cases, non-uniform treatment of fluid.

Accordingly, while the above-described prior art systems have been successful, the present inventor has been concerned with improving fluid treatment devices and systems to overcome some of these disadvantages. The present invention will now be described with reference to the remaining Figures.

Figure 2:
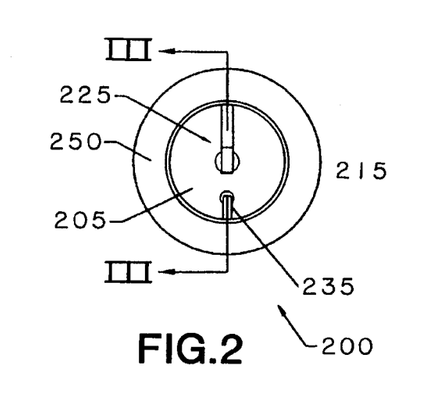
FIG. 2 illustrates an end view of a first embodiment of a fluid treatment device in accordance with the present invention.
Figure 3:
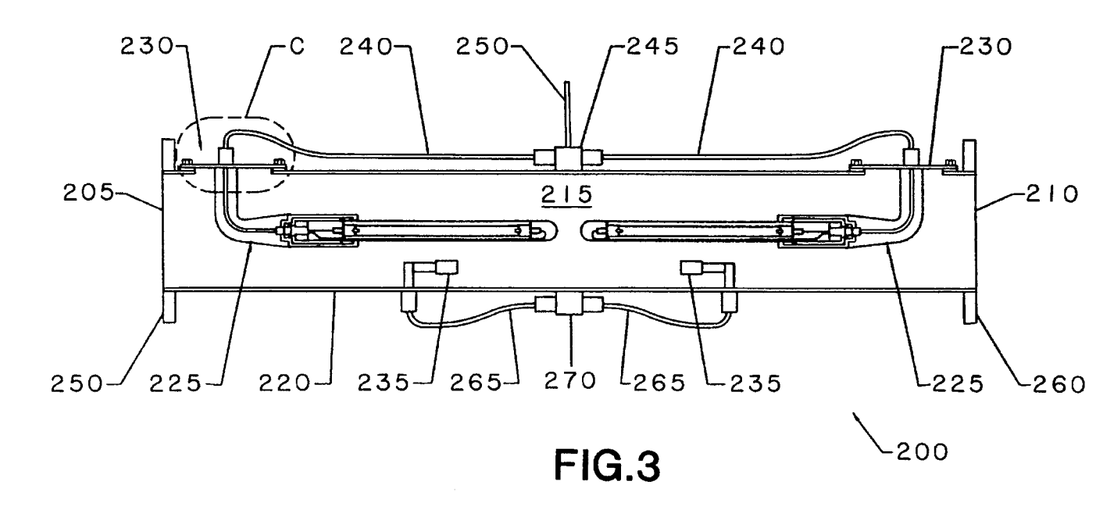
FIG. 3 illustrates a section along line III—III in FIG. 2.

With reference to FIGS. 2 and 3, there is illustrated a fluid treatment system 200 comprising a fluid inlet 205, a fluid outlet 210 and a fluid treatment zone 215 disposed in a housing 220. Disposed in housing 220 are two radiation source modules 225. Each radiation source module 225 is mounted to housing 220 by a mounting plate 230 which will be described in more detail hereinbelow. Also disposed in housing 220 are two radiation sensors 235. Emanating from each radiation source module 225 is an electrical lead 240. Each of the electrical leads 240 enters a junction box 245 from which a main electrical conduit 250 emanates. Fluid inlet 205 includes an inlet flange 255 and fluid outlet 210 includes an outlet flange 260. Emanating from each radiation sensor is an electrical lead 265. Each of the electrical leads 265 enters a junction box 250 from which a main electrical conduit (not shown) emanates.

Ideally, fluid treatment system 200 is constructed to be used in-line in existing fluid (e.g. water) piping. Thus, for a given installation, it is desirable to design fluid treatment zone 215 such that it has substantially the same cross-sectional shape and dimension as the existing piping. Inlet flange 255 and outlet flange 260 can be used to facilitate installation of fluid treatment system 200 between mating flanges in the existing piping. When the systems is installed, it will be apparent to those of skill in the art that fluid flow through fluid treatment zone 215 is parallel with respect to the lamps disposed in radiation source module 225. This minimizes the occurrence of hydraulic headloss in the flow of fluid and eliminates dead zones resulting in more efficient treatment of the fluid.

Figures 4, 5:
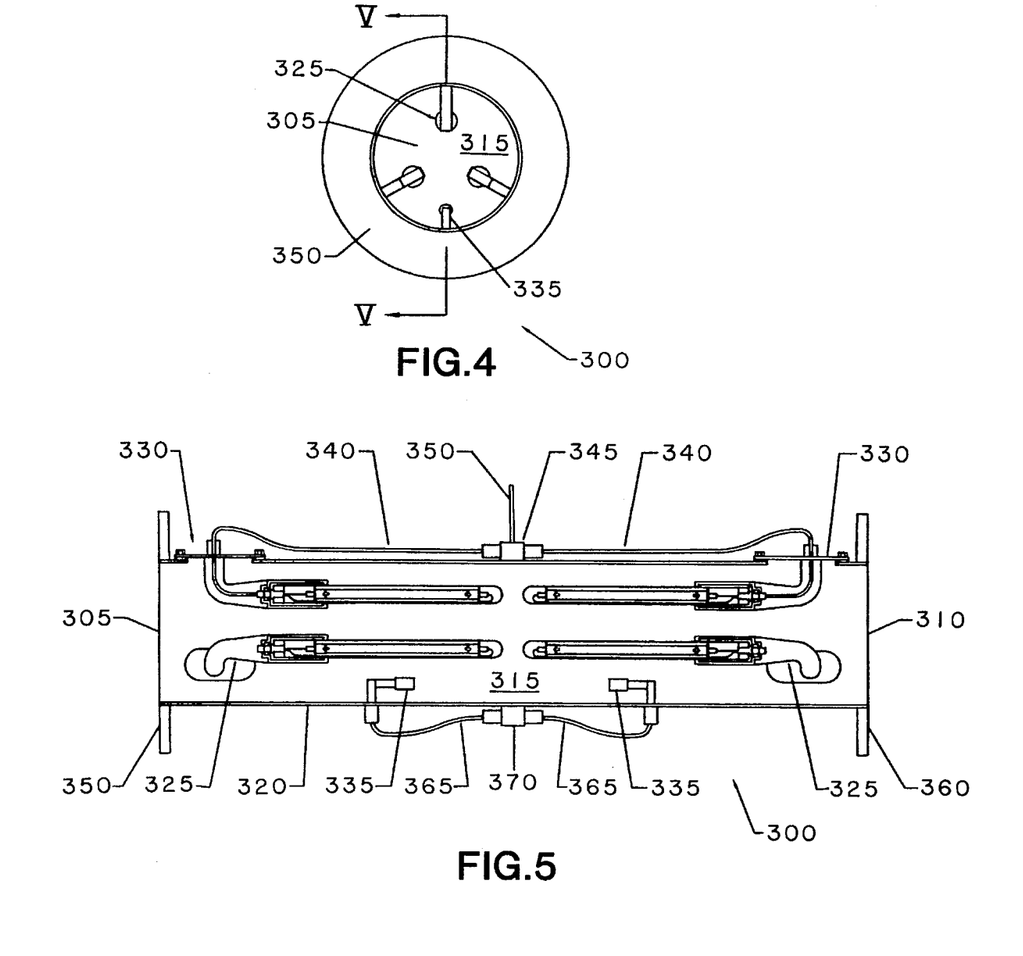
FIG. 4 illustrates an end view of a second embodiment of a fluid treatment device in accordance with the present invention.
FIG. 5 illustrates a section along line V—V in FIG. 4.

With reference to FIGS. 4 and 5, there is illustrated a fluid treatment system 300 comprising a fluid inlet 305, a fluid outlet 310 and a fluid treatment zone 315 disposed in a housing 320. Disposed in housing 320 are six radiation source modules 325. Each radiation source module 325 is mounted to housing 320 by a mounting plate 330 which will be described in more detail hereinbelow. Also disposed in housing 320 are two radiation sensors 335. Emanating from each radiation source module 325 is an electrical lead 340. Each of the electrical leads 340 enters a junction box 345 from which a main electrical conduit 350 emanates. Fluid inlet 305 includes an inlet flange 350 and fluid outlet 310 includes an outlet flange 360. Emanating from each radiation sensor is an electrical lead 365. Each of the electrical leads 365 enters a junction box 370 from which a main electrical conduit (not shown) emanates.

Figure 6:
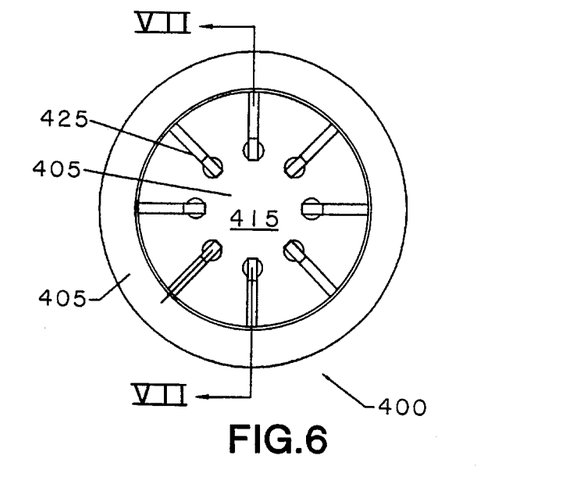
FIG. 6 illustrates an end view of a third embodiment of a fluid treatment device in accordance with the present invention.
Figure 7:
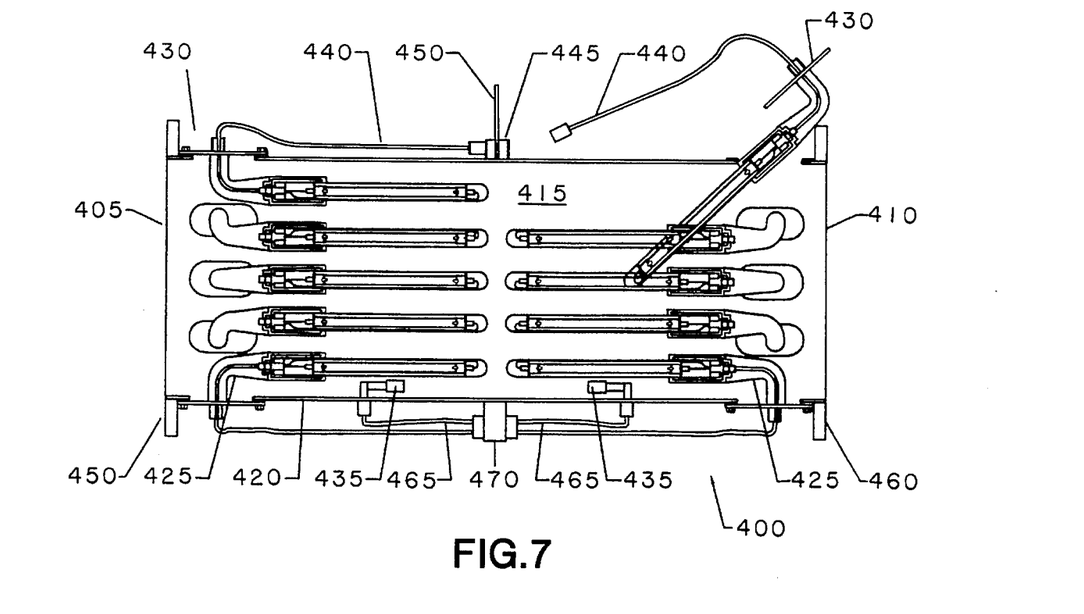
FIG. 7 illustrates a section along line VII—VII in FIG. 6.

With reference to FIGS. 6 and 7, there is illustrated a fluid treatment system 400 comprising a fluid inlet 405, a fluid outlet 410 and a fluid treatment zone 415 disposed in a housing 420. Disposed in housing 420 are sixteen radiation source modules 425. Each radiation source module 425 is mounted to housing 420 by a mounting plate 430 which will be described in more detail hereinbelow. Also disposed in housing 420 are two radiation sensors 435. Emanating from each radiation source module 425 is an electrical lead 440. Each of the electrical leads 440 enters a junction box 445 from which a main electrical conduit 450 emanates. Fluid inlet 405 includes an inlet flange 450 and fluid outlet 410 includes an outlet flange 460. Emanating from each radiation sensor is an electrical lead 465. Each of the electrical leads 465 enters a junction box 470 from which a main electrical conduit (not shown) emanates.

The construction and use of the fluid treatment systems 300 (FIGS. 4 and 5) and 400 (FIGS. 6 and 7) may be effected in the same manner as discussed hereinabove for fluid treatment system 200 (FIGS. 2 and 3).

Figure 8:
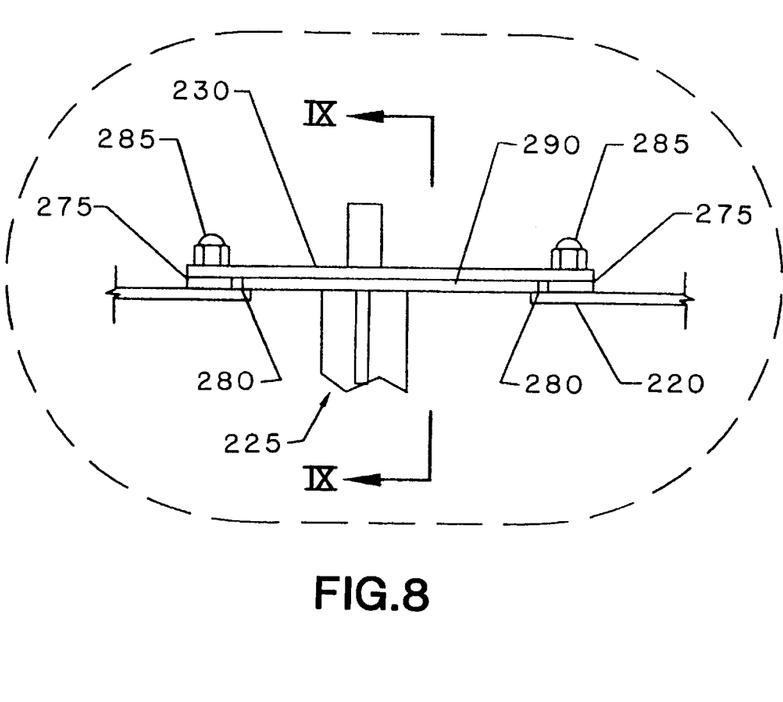
FIG. 8 illustrates is an expanded view of the area designated C in FIG. 3.
Figure 9:
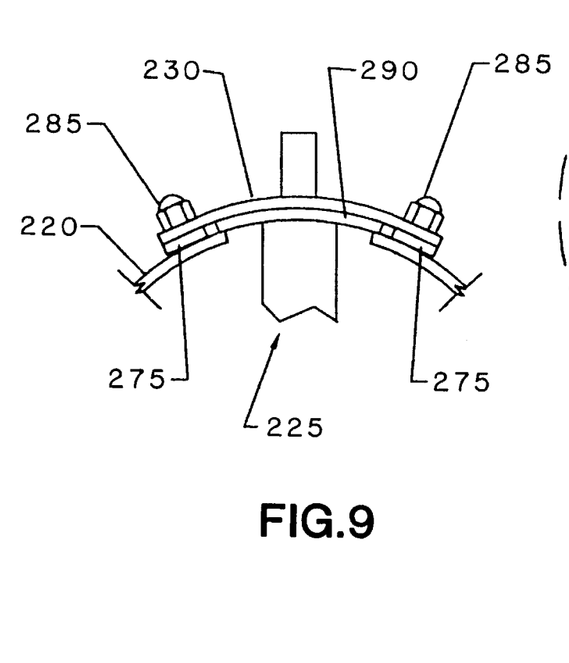
FIG. 9 illustrates is section along line IX—IX in FIG. 8.

With reference to FIGS. 8 and 9, mounting plate 230 is affixed to housing 220 in the following manner. Initially, it will be apparent that housing 220 comprises a suitably shaped aperture to receive each radiation source module 225. The shape of the aperture is preferably similar to that of mounting plate 230 and the size of the aperture is smaller than that of mounting plate 230. A flange ring 275 sized larger than and having the same shape as the aperture is affixed to housing 220 to define a notch in which a resilient O-ring 280 is placed. Flange ring 275 has a plurality of upstanding bolts (not shown). Mounting plate 230 has a plurality of complementary apertures to receive the bolts on flange ring 275. Mounting plate 230 also contains a backup plate 290 to form, together with flange ring 275, a cavity for O-ring 280. Torque bolts 285 are in threaded engagement with each of the upstanding bolts on flange ring 275.

Thus, with reference to FIGS. 2, 3, 8 and 9, radiation source module is installed in the following manner (see also FIG. 7). The end of radiation source module distal mounting plate 230 is inserted in an aperture in housing 220. Mounting plate 230 is then positioned by ensuring that the apertures therein receive the upstanding bolts on flange ring 275. Torque nuts 285 are then tightened with sufficient force to compress O-ring 275 thereby providing a hermetic seal between fluid treatment zone 215 and the exterior of housing 220.

Figure 10:
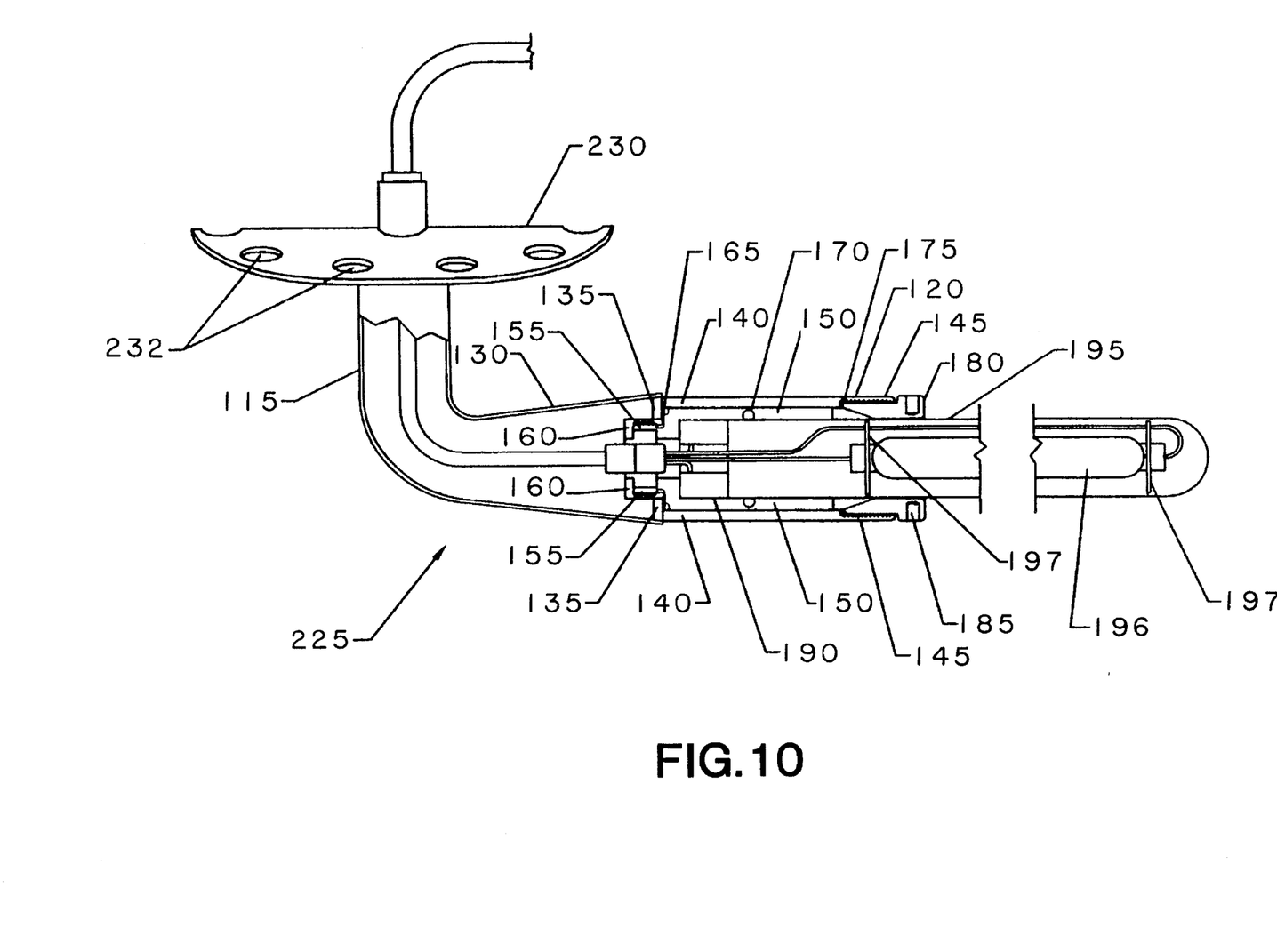
FIG. 10 illustrates a side elevation, partially cut away, of a radiation source module used in the devices illustrated in FIGS. 2–9.

With reference to the FIG. 10, there is illustrated a detailed view of a radiation source module 225. It will be appreciated by those of skill in the art the radiation source module 225 is similar to radiation source modules 325 (FIGS. 4 and 5) and 425 (FIGS. 6 and 7). There is detailed discussion of such a module in copending U.S. patent application Ser. No. 08/325,949, in the name of the present inventor and filed on even date herewith and hereby incorporated by reference. Thus, radiation source module comprises a support member 115, a radiation source assembly 120 extending from support member 115 and mounting plate 230 for affixing radiation source module 225 to housing 220. Mounting plate 230 has a plurality of apertures 232 which receive upstanding bolts from flange ring 275 (FIGS. 2, 3, 8 and 9).

Radiation source assembly 120 includes a concentric reducer 130 which can be welded to or made integral with support member 115. Affixed to concentric reducer 130 is a ring 135 to which is affixed a mounting sleeve 140. The end of mounting sleeve 140 distal concentric reducer 130 has a threaded portion 145. Disposed within mounting sleeve 140 is an inner sleeve 150 having a threaded portion 155 to which is engaged a cap nut 160. Inner sleeve 150 comprises suitable notches to receive a pair of resilient O-rings 165, 170. The end of inner sleeve 150 distal concentric reducer 130 abuts a resilient, tapered sealing ring 175. A threaded mounting nut 180 engages threaded portion 145 of mounting sleeve 140 and abuts tapered sealing ring 175. Threaded mounting nut 180 is provided with torquing receptacles 185 which receive a suitable tool useful for torquing mounting nut 180 into sealing engagement with mounting sleeve 140.

Disposed within inner sleeve 150 is an annular piezo-electric ceramic transducer 190 which is a laminate structure made up of a plurality of individual annular piezo-electric ceramic transducers (not shown) adhered together. One end of transducer 90 abuts inner sleeve 150 and the other end of transducer 190 abuts, either directly or indirectly, the open end of a quartz sleeve 195. As illustrated, the opposite end of quartz sleeve 195 is closed. Disposed within quartz sleeve 195 is a radiation source 196. Ideally, the radiation source is an ultraviolet lamp. The ultraviolet lamp is not particulary restricted and the choice thereof is within the purview of a person skill in the art. A pair of spacers 197 are disposed within quartz sleeve 195 and serve to centre and hold in place radiation source 196 within quartz sleeve 195. The electrical connection and control of radiation source 196 is conventional and within the purview of a person skilled in the art.

As described in incorporated copending U.S. patent application Ser. No. 08/325,949, filed on even date herewith, radiation source module 225 is self-cleaning by intermittent or continuous operation of transducer 190 during irradiation of the flow of fluid. More specifically, operation of transducer 190 results in reciprocal vibration of quartz sleeve 195 in a direction substantially parallel to the elongate axis of quartz sleeve 195. Such vibration may be effected by utilizing a piezo-electric transducer, preferably a piezo-electric ceramic transducer. Piezo-electric ceramic transducers have been conventionally used in sonar applications. A suitable piezo-electric ceramic transducer useful in the present radiation source module is commercially available from EDO Corporation (Salt Lake City, Utah) and consists essentially of a ceramic component which meets the specifications of U.S. Navy Type 1 (I) or U.S. Navy Type 3 (III). As will be apparent to those of skill in the art, a ceramic meeting the specifications of U.S. Navy Type 1 is a hard lead zirconate titanate with a Curie point greater than about 310° C. and a ceramic meeting the specifications of U.S. Navy Type 3 is a very hard lead zirconate titanate with a Curie point greater than about 290° C. Detailed specifications of these ceramic specifications can be found in published Department of Defense Military Standard DOD-STD 1376A(SH), dated Feb. 28, 1984, the contents of which are hereby incorporated by reference. Generally, the piezo-electric transducer, most preferably an annular piezo-electric transducer, is one which can be operated at a frequency in the range of from about 1 kHz to about 100 kHz, preferably from about 10 kHz to about 20 kHz, more preferably about 10 kHz to about 15 kHz.

Of course it will be appreciated by those of skill in the art that the illustrated embodiments of the radiation source module may be varied to suit the particular fluid treatment system without departing from the spirit of the invention. For example, the number, type and arrangement of sealing rings (i.e. O-rings, tapered rings, etc.) can be varied while maintaining a hermetic seal. Further, the use of in situ means to clean the radiation source module is option. If in situ means to clean the radiation source module is used, it may be a device other than the vibration cleaning device described hereinabove. It should be understood that, while exemplary embodiments of the present invention have been described herein, the present invention is not limited to these exemplary embodiments and that variations and other alternatives may occur to those of skill in the art without departing from the intended spirit and scope of the invention as defined by the attached claims.

What is claimed is:

1. A fluid treatment device comprising a housing for receiving a flow of fluid, the housing comprising a fluid inlet, a fluid outlet, a fluid treatment zone disposed between the fluid inlet and the fluid outlet, and at least one radiation source module disposed in the fluid treatment zone, the at least one radiation source module being removable through an aperture provided in the housing intermediate the fluid inlet and fluid outlet, the at least one radiation source module comprising a radiation source sealably connected to a leg, the leg sealably mounted to the housing, the radiation source being disposed substantially parallel to the flow of fluid.

2. The fluid treatment device defined in claim 1, wherein the fluid inlet, the fluid outlet and the fluid treatment zone have substantially the same cross-section.

3. The fluid treatment device defined in claim 1, wherein the fluid inlet, the fluid outlet, and the fluid treatment zone are arranged in a substantially collinear manner.

4. The fluid treatment device defined in claim 1, wherein the housing is a substantially elongate cylinder.

5. The fluid treatment device defined in claim 1, wherein the housing has a substantially circular cross-section.

6. The fluid treatment device defined in claim 1, wherein the at least one radiation source module comprises at least one ultraviolet lamp.

7. The fluid treatment device defined in claim 6, wherein the at least one radiation source module further comprises a sleeve disposed about a portion of the exterior of the at least one ultraviolet lamp.

8. The fluid treatment device defined in claim 1, further comprising cleaning means to remove undesired materials from the exterior of the at least one radiation source module.

9. The fluid treatment device defined in claim 1, further comprising means to monitor the level of radiation being emitted from the radiation source.

10. The fluid treatment device defined in claim 1, wherein the leg comprises a conduit for carrying electrical connection means to the radiation source.

11. The fluid treatment device defined in claim 1, wherein the end of the leg distal the radiation source comprises a mounting plate sealably connected to the housing.

12. The fluid treatment device defined in claim 1, comprising a plurality of radiation source modules mounted circumferentially to the housing to define a radiation source ring.

13. The fluid treatment device defined in claim 12, wherein the radiation source modules are arranged substantially equidistant to one another.

14. The fluid treatment device defined in claim 12, comprising two or more radiation source rings.

15. A method of treating a fluid in a housing comprising a fluid inlet, a fluid outlet, a fluid treatment zone disposed between the fluid inlet and the fluid outlet, the fluid treatment zone having at least one radiation source disposed therein, the method comprising the steps of:

(i) providing a flow of the fluid to the fluid inlet;

(ii) feeding the flow of fluid from the fluid inlet to the fluid treatment zone in a manner substantially parallel to the at least one radiation source;

(iii) irradiating the flow of fluid in the fluid treatment zone;

(iv) subjecting a surface of the at least one radiation source in contact with fluid to reciprocal vibration to remove undesired materials from the surface;

(v) feeding the flow of fluid to the fluid outlet;

wherein the flow of fluid through the fluid inlet, the fluid outlet and the fluid treatment zone is substantially collinear.

16. The method defined in claim 15, comprising the further step of selecting the fluid inlet, the fluid outlet and the fluid treatment zone having substantially the same cross-section.

17. The method defined in claim 15, wherein the housing is a substantially elongate cylinder.

18. The method defined in claim 15, wherein the housing has a substantially circular cross-section.

19. The method defined in claim 15, wherein the at least one radiation source comprises at least one ultraviolet lamp.

20. The method defined in claim 19, wherein the at least one radiation source further comprises a sleeve about a portion of the exterior of the at least one ultraviolet lamp.

21. The method defined in claim 15, wherein the fluid comprises water.

22. The method defined in claim 15, comprising the further step of monitoring the level of radiation being emitted from the radiation source.

23. The fluid treatment device defined in claim 7, further comprising vibration generation means in contact with the sleeve, the vibration generation means capable of effecting reciprocal vibration of the sleeve to remove undesired materials from the sleeve.

24. The fluid treatment device defined in claim 23, wherein the vibration generation means comprises a piezo-electric transducer.

25. The fluid treatment device defined in claim 24, wherein the piezo-electric transducer has an operating frequency of from about 1 kHz to about 100 kHz.

26. The fluid treatment device defined in claim 24, wherein the piezo-electric transducer has an operating frequency of from about 10 kHz to about 20 kHz.

27. The method defined in claim 15, wherein reciprocal vibration is conducted at a frequency of from about 1 kHz to about 100 kHz.

28. The method defined in claim 15, wherein reciprocal vibration is conducted at a frequency of from about 10 kHz to about 20 kHz.

* * * * *